United States Patent [19]

Poley

[11] Patent Number: 4,911,714
[45] Date of Patent: Mar. 27, 1990

[54] FOLDABLE INTRAOCULAR LENS AND IMPROVED FOLD RETAINING MEANS

[76] Inventor: Brooks J. Poley, 2 Greenway Gables, Minneapolis, Minn. 55403

[21] Appl. No.: 213,325

[22] Filed: Jun. 30, 1988

Related U.S. Application Data

[63] Continuation-in-part of Ser. No. 31,250, Mar. 26, 1987, Pat. No. 4,769,034.

[51] Int. Cl.⁴ ............................................... A61F 2/16
[52] U.S. Cl. ....................................................... 623/6
[58] Field of Search ......................... 623/6; 128/303 R

[56] References Cited

U.S. PATENT DOCUMENTS

| | | |
|---|---|---|
| 4,451,938 | 6/1984 | Kelman . |
| 4,527,294 | 7/1985 | Heslin ..................................... 623/6 |
| 4,562,600 | 1/1986 | Glusberg ................................. 623/6 |
| 4,573,998 | 3/1986 | Mazzocco . |
| 4,605,409 | 8/1986 | Kelman ................................... 623/6 |
| 4,636,210 | 1/1987 | Hoffer . |
| 4,681,102 | 7/1987 | Bartell ............................. 128/303 R |

OTHER PUBLICATIONS

"The Second Generation Small Incision Silicone IOL", from Allergan Medical Optics.

"Soft IOL Technology: The New Frontier", by V. L. Bohn, Ocular Surgery News, vol. 5, No. 5, 3/1/87.

"Pathologic Findings of an Explanted Silicone Intraocular Lens", by Donald A. Newman, M.D., et al., *J. Cataract Refract. Surg.*, vol. 12, May 1986, p. 292.

"Implantation Procedure for the Bechert 7 mm One-Piece Posterior Chamber Lens", by Chas. H. Bechert, M.D., Precision-Cosmet Co., Inc.

Primary Examiner—Richard J. Apley
Assistant Examiner—James Prizant
Attorney, Agent, or Firm—Wood, Herron & Evans

[57] ABSTRACT

A foldable intraocular lens is releasably retained in folded configuration for implanting, by suturing through apertures adjacent its peripheral edge, or by structure which is integral with the lens. An elongated lens is disclosed, wherein the retaining means and haptics are located on extended upper and lower ends of the lens, out of the field of vision.

6 Claims, 3 Drawing Sheets

FOLDABLE INTRAOCULAR LENS AND IMPROVED FOLD RETAINING MEANS

This application is a continuation-in-part of my copending application Ser. No. 07/031,250, filed Mar. 26, 1987, titled "Method of Implanting Folded Intraocular Lens", which is now U.S. Pat. No. 4,769,034, issued Sept. 6, 1988.

FIELD OF THE INVENTION

This invention relates generally to the implanting of intraocular lenses, and more specifically to a lens which can be temporarily folded to a smaller size for implanting it; releasable retaining means for holding the lens in the folded configuration for implanting; and a method for securing and implanting the lens in the folded configuration and then unfolding it within the eye.

BACKGROUND OF THE INVENTION

In my earlier copending application identified above, there is disclosed a method of implanting an intraocular lens wherein the effective width of the lens is reduced for implantation by folding the lens and fastening a flexible retainer about it for insertion and then, when the lens has been implanted in the eye, releasing the retainer to free the lens so that the lens can be unfolded within the eye. Apparatus for folding the lens and a retainer for temporarily securing the lens in the folded configuration are also disclosed. The folded lens can be inserted through a much smaller incision than would otherwise be required. For example, a lens which is the typical 6.5 mm in diameter in the unfolded state has an effective width when singly folded of only about 3.2 mm (measured transversely to the axis of folding).

The fold retaining means or "retainer" disclosed in my earlier application may be formed of a thin, flexible material and can be applied around the lens, like a releasable band. Because of its thinness the retainer does not add substantially to the effective diameter of the folded lens, yet it holds the lens so that the lens can be inserted into the eye through a smaller incision.

Experimentation with intraocular lenses held folded by a retainer of the preferred type illustrated in my earlier application has demonstrated that the retainer functions effectively and that, once applied to a lens, the retainer can satisfactorily be removed and the lens unfolded within the eye. However, a practical difficulty has been encountered in that it has been found difficult, or at least time consuming, to apply the retainer to the folded lens prior to implanting, without considerable practice.

My earlier application also discloses an apparatus which is useful to fold a lens so that a retainer can be tied manually "on site", that is, by the physician prior to implanting it. However, the small size and resiliency of the lens makes the placing and securing of the retainer on the lens relatively slow for someone who has not had previous experience in doing so. Accordingly, that application contemplates that the retainer will often be applied by the lens manufacturer and the lens supplied to the eye surgeon in the folded configuration with the retainer already in place, ready for use.

However, some types of plastic materials used to make such foldable lenses tend gradually to lose their resiliency over a period of time and, if held folded by a restrainer for an indefinitely long period of time, such lenses might tend to become deformed so that they would not fully unfold to the original shape but rather would retain some unwanted curvature from folding. This consideration raised the possibility that a lens held folded by a retainer might not have an adequately long shelf life for distribution in the usual channels. Hence it is desirable to provide a means and method by which a lens which could be folded and secured in folded configuration by the physician or an assistant at the point and time of use, i.e., shortly prior to the actual implant operation. In short, there is a need for a simpler way of retaining a lens in a folded configuration, yet which enables the lens to be readily be unfolded and positioned after it has been inserted in the eye.

THE PRIOR ART

A rigid (non-foldable) oval intraocular lens is known, having a minor diameter of about 5 mm and a major diameter of about 6.5 mm. The smaller minor diameter enables the lens to be inserted through a smaller incision than is required for the usual circular type of rigid lens. However, to provide peripherally unobstructed sight through it, an intraocular lens must ave a circular field of vision of at least abut 6.5 mm diameter. The small minor diameter of the prior art oval lens therefore does not provide an adequate field, and vision is thereby somewhat impaired, particularly if the lens becomes decentered. The lens is rigid and cannot be folded; it is inserted so that it passes longways through the incision, and its major axis is oriented vertically in use.

Mazzocco U.S. Pat. No. 4,573,998 teaches methods for implanting folded lenses or rolled up intraocular lenses, using a special injector-like tool for the purpose.

Kellman U.S. Pat. No. 4,605,409 discloses a lens which has foldable masks or "wings" on opposite sides of the optical viewing area of the lens. The patent suggest that the masks can be folded inwardly for insertion and held in the contracted condition by the use a suture, which is not shown or further described.

SUMMARY OF THE INVENTION

The present invention provides a lens and several embodiments of folded lens retaining means which can be secured more easily than those disclosed in my earlier application.

In the preferred embodiment of the lens with retaining means, a resilient lens is folded in half about a central axis of folding, like a taco, so that the two halves of the lens on either side of the axis of folding facially overlie one another. (Of course the fold should not be creased, in order to avoid a possibility of causing permanent deformation.) Corresponding opposite edge portions of the lens are thereby juxtaposed. A length of flexible material (which may be similar to and is broadly referred to hereinafter as a "suture"), is passed through apertures on both halves of the lens which may be formed by piercing the juxtaposed edge portions as with a suturing needle. The suture can be tied upon itself as in conventional suturing; or it may be knotted or otherwise provided with one or more enlarged "stops" outside the lens, so that no loop is formed and only a single length of suture is held in tension.

I have discovered that it is readily feasible, as an on-site manipulative technique, for a physician to fold the lens, pierce its opposite halves with a conventional suture needle, form the suture into a loop, draw up the suture and tie it on itself, following much the same practice as is used to suture skin. I have further found that resilience of conventional foldable lens material is such that the lens tends to flare or "funnel" outwardly on each side of the point at which it is secured together. This makes it easier to sever and release the suture or other retaining means within the eye without cutting or nicking the lens surface. One end of the suture may extend outside the eye to facilitate removal of the suture once cut loose.

In another embodiment a lens is formed with integral latching means such as a catch or a T-shaped handle extending from one side. The latch is engageable with a cooperating slot or seat on a diametrically opposite side of the lens, to hold the lens folded. Both the latch and the slot can be formed integrally with the lens; separate latching means is not required in this embodiment. Further, the latching means may remain with the lens in the eye after the lens has been implanted.

Each of these retaining means can easily be applied or secured just prior to the actual implantation of the lens. Each type of retainer can be released within the eye and the lens unfolded, by using a variant of the method of my earlier application.

In another aspect of the invention, a vertically "elongated" lens is provided which has an unobstructed, circular central vision area which is large enough (i.e., its diameter is sufficient) to provide an unobstructed field of vision through the lens are implanted, even if some decentering occurs. The lens has elongated end portions which are contiguous with the vision area, and which are so positioned that, when implanted, the end portions are above and below the vision area. The major or long axis of the lens extends through the end portions and in use will be parallel to the patient's spine. The end portions provide mounting areas for haptics, so that the points at which the haptics join the lens lie outside the field of vision. If used, apertures and/or other retaining means can also be positioned in the end areas, preferably midway between the long (major) and short (minor) axes of the lens, so that they are outside the viewing area, i.e., the optically active region of the lens. The apertures or other retaining means, even if they remain attached to the lens after it has been implanted and unfolded, do not interfere with vision because they are outside the center area through which light is focused on the retina. This lens construction provides an advantage whether or not any retaining means is used; when folded it can be inserted through a smaller aperture, however retained in the folded configuration, than a rigid lens could be.

Because the folded lens has a much smaller width than the corresponding unfolded lens, the technique of this invention is especially usable following phako-emulsification for removing a cataract, although it is not limited to such use. The incisions used in phako-emulsion can be as small as approximately 3.2 mm in width; the folded lens of this application can be inserted through an incision of that size.

A "two instrument" technique is preferred for inserting the lens and positioning it within the eye, wherein the lens is gripped with one instrument for implanting through a first or primary surgical incision, and once inserted into the eye, is released, unfolded and positioned with a second instrument inserted through a smaller secondary surgical incision angularly offset from the first. The second instrument is used to sever the suture or otherwise release the lens from the retaining means, and to control the unfolding of the lens.

DESCRIPTION OF THE DRAWINGS

The invention can best be further described by reference to the accompanying drawings, in which.

DETAILED DESCRIPTION

Figure 1:
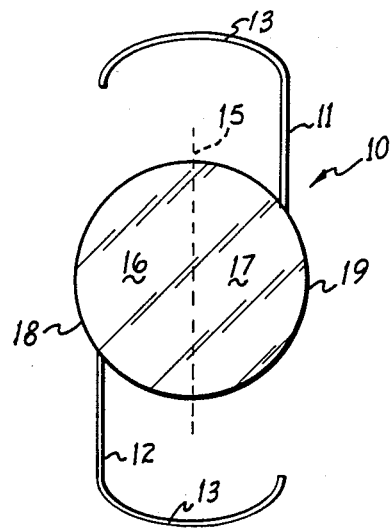
FIG. 1 is an enlarged plan view of one type of foldable intraocular lens, with which the invention can be practiced.
Figure 10:
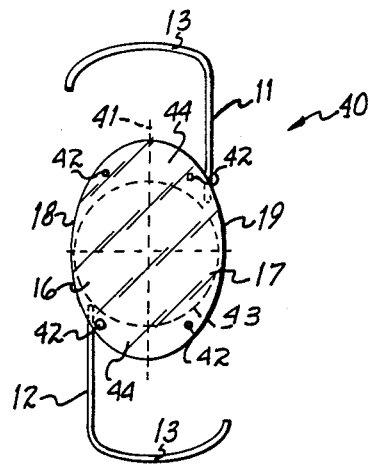
FIG. 10 is a plan view of a lens which is elongated in shape, and which has preformed apertures for retaining by a suture.

The invention can be practiced with various types of foldable lenses. FIG. 1 illustrates a commercially available type of lens which is suitable for use in the invention, while FIG. 10 shows a new type of lens having both an unusual shape and an integral retaining means in accordance with the invention.

The commercially available lens indicated at 10 in FIG. 1 is circular in outline and has a conventional lens sectional shape with two haptics 11 and 12 that extend angularly from it at opposite points. The particular lens shown is of the general type sold by Allergan Medical Optics Division of Allergan, Inc. of Irvine, Calif., under their designation "Second Generation Small Incision Silicon I.O.L." and is designed to be foldable. The two haptics 11 and 12 are flexible and hook-shaped, having shanks which are parallel to one another but offset laterally. Each haptic has a hook-shaped end portion 13, and it will be noted that in the unfolded configuration the end portion 13 of the upper haptic 11 extends to the left whereas that of the lower haptic 12 extends to the right; that is, the hooks extend in opposite directions. As will be described, when the lens is folded both haptics extend in the same direction.

Figure 2:
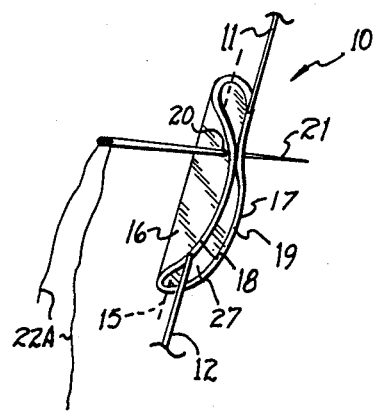
FIG. 2 is a diagrammatic perspective showing a preferred method of suturing the lens of FIG. 1 to hold it folded.

The lens 10 is made of a resiliently foldable flexible material, for example a silicone composition, whereby it can be folded along a axis of folding which, in the preferred form, is a transverse central axis midway between the shanks of the haptics 11, 12, as indicated by the dotted line 15 in FIGS. 1 and 2.

For use in the presently preferred embodiment of the invention, the lens is folded in half about the axis of folding, as illustrated in FIG. 2. This can be done with the fingers, or a folding apparatus can be used, for example as shown in my previously identified parent application.

Folded in such configuration, the two halves of the lens 16 and 17 facially overlie one another, and corresponding lens edge portions 18 and 19 are juxtaposed. The lens halves 16 and 17 are sutured together adjacent their edge portions 18 and 19, which may be done by the use of a common suture needle 21 and sutures 22A and 22B (FIGS. 2 an 3). The needle may for example be an Ethicon needle #7770; the suture material may be 9-0 nylon. Surprisingly, I have found that the lens can be sutured without ripping, even though the suture is positioned very close to the periphery of the lens, for example 1 to 2 mm from the edge. The apertures 20 for the suture can be formed with the needle; or they can be preformed by the lens manufacturer.

Figure 3:
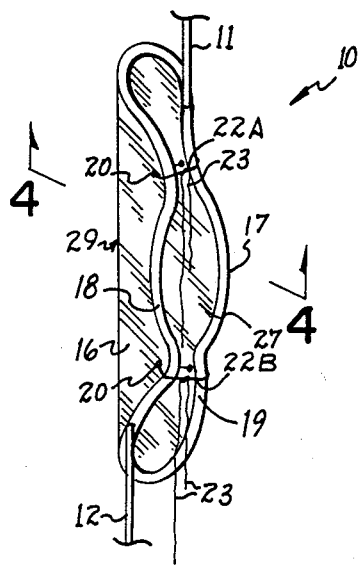
FIG. 3 is an enlarged perspective of a lens of the type shown in FIGS. 1 and 2, doubly sutured.
Figure 4:
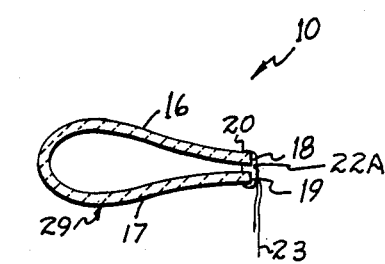
FIG. 4 is a cross-section taken on line 4—4 of FIG. 3.

To secure the lens the suture can be looped and drawn up on itself, as shown in FIG. 4. The lens is preferably sutured at two positions (see FIG. 3). An elongated tail may be left on the suture, by which the suture can be withdrawn from the eye after it has been severed.

Figure 5:
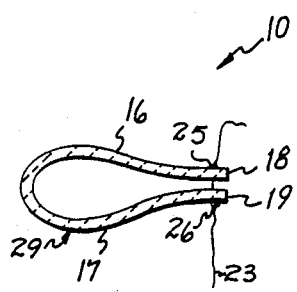
FIG. 5 is a cross-section, similar to FIG. 4 but shows a folded lens retained with a suture secured in a different way.

FIG. 5 shows an alternative method of securing the suture according to which, instead of tying the suture as a loop, the suture is provided with enlarged knots or stops 25, 26 on the outside of the folded lens. These abut the outside of the lens, on opposite sides of it, and prevent it from unfolding. These can be figure of eight knots or other enlarged stops of sufficient diameter to prevent them slipping from through the apertures 20 in the lens.

As shown in FIG. 2 and 3, the folded lens has a taco-like shape, and adjacent the sutures 22A and 22B or other securing means the lens halves 1 and 17 flare or funnel outwardly, away from the securing means, as indicated at 27. For reasons described in more detail below, a funnel shape of the lens adjacent the securing means facilitates cutting the suture or releasing the retaining means after the lens has been implanted.

FIGS. 6–9 illustrate the sequence of steps in implanting and releasing a doubly sutured lens 29 of the type shown in FIG. 3. For purposes of the following discussion, it is assumed that a phako emulsification has been performed, although it should be understood that this implantation technique is useful whether or not a cataract has been removed and regardless of the particular technique by which the cataract is removed.

Figure 6:
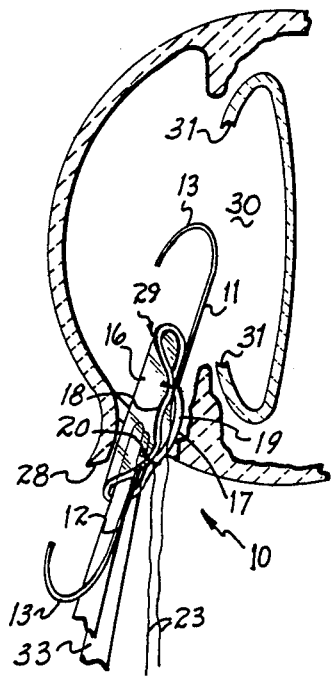
FIG. 6 is an enlarged diagrammatic section showing the implantation of a doubly sutured lens into a human eye.
Figure 7:
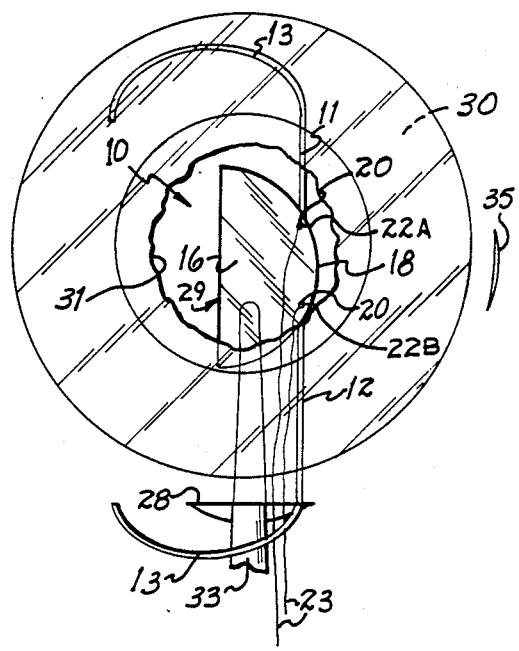
FIG. 7 is a diagrammatic plan view similar to FIG. 6, but shows the folded lens after it has been inserted into an eye, before the retaining means has been released.
Figure 8:
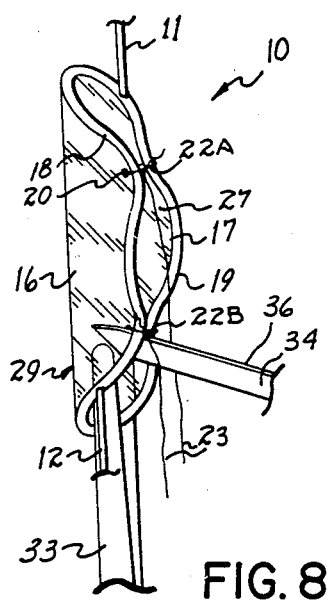
FIG. 8 is a diagrammatic perspective of the sutured lens as the first suture is being cut.

Referring to FIG. 6, after a cataract has been removed, the preferred technique is a two incision technique in which the folded lens 29 is inserted through a primary surgical incision 28. Phakoemulsification requires an opening which is about 3.2 mm or slightly larger, accordingly, incision 28 may be formed to just the width required for the phako emulsification tool to be inserted. The opening need not be enlarged to accept the full diameter of the folded lens or the haptics. The folded lens is inserted longitudinally, haptic 11 first, through incision 28 into the lens capsule pocket 30 which has already been cut away in accordance with conventional procedure which leaves a pocket edge 31. The lens is held for such insertion by a first surgical instrument, suitably a forceps 33, adjacent the axis of folding. The lens is held by the forceps 33 which grips the lower lens half, i.e., the lens half 17 in FIGS. 6–9. The hook end 13 of haptic 12 remains outside the incision until the lens has been unfolded. Reference may be had to my previously identified co-pending application, the disclosure of which is incorporated by reference in its entirety herein, for further details of the method of inserting folded lenses. FIG. 7 illustrates the orientation of a folded lens of the FIG. 1 type after it has bee inserted but before it has been unfolded. It will be seen that the ends 13 of both haptics are now facing the same direction, that is, to the left in FIG. 7.

Figure 9:
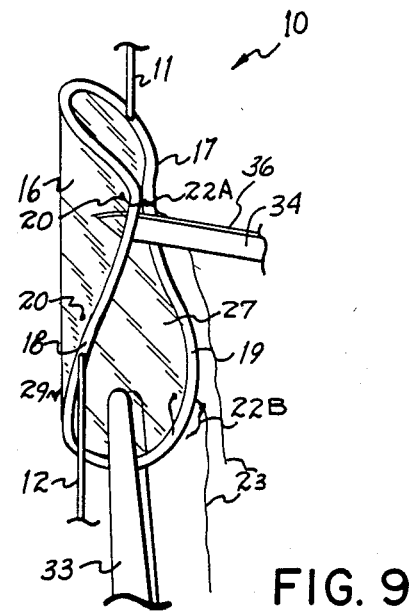
FIG. 9 is a view similar to FIG. 8 but shows the lens as the second suture is being cut.

After the lens has been inserted and the upper haptic 11 has been seated in lens pocket 30, the lens is unfolded. In the preferred technique this is done with a second surgical instrument 34, which is inserted through a secondary incision 35 (see FIG. 7). The second instrument 34 is preferably a flat bladed knife having a sharpened edge 36, although it could alternatively be a scissors or a knife with a hook-shaped distal end with a sharp edge on the inside of the hooked end. It can be seen in FIG. 8 that the flare or funnel shape 27 of the folded lens, adjacent the sutures, facilitates cutting the sutures without nicking or damaging the lens surface. The lens is held by forceps 33 during this procedure. After one suture 22B has been cut, the other suture 22A is cut in like fashion with instrument 34 (FIG. 9). Thereafter knife 34 can be removed and the two sutures removed through opening 28. The tail 23 of each suture is preferably long enough that it extends outside the eye through incision 28 for removal (FIG. 7).

As the sutures are cut the lens tends to unfold spontaneously, that is, the lens half 16 tends to turn to the left in FIG. 9. To prevent the edge 19 of this half from scraping the inside of the cornea, unfolding of the lens can be controlled with the instruments 33 and 34. The lens is preferably pushed somewhat inwardly, into the pocket, to provide clearance for lens edge portion 19 so that it does not contact the cornea as it unfolds; and/or the unfolding can be controlled and slowed with second instrument 34, by holding the innermost lens half 17 inwardly to prevent the outer lens half from contacting the cornea. As the lens unfolds, the end 13 of haptic 12 which faces toward the left in FIG. 7, rotates with left lens half 16, its hook end 13 being free to rotate outside the eye. The unfolded lens is then centered within the eye and haptic end 13 is seated within pocket 30.

In he technique described, the lens is folded about a single axis of folding and two sutures are passed through the lens at positions adjacent the overlying lens edge portions. While it would be possible to fold the lens in thirds about two parallel axes of folding, this does not appear necessary and makes suturing and unfolding more difficult. It is not, therefore, the preferred practice at present.

Where the suture is single loop, as in the configuration shown in FIG. 4, either side of the loop (either between the apertures or outside the lens) may be cut to release it. In the less preferred configuration of FIG. 5 wherein the suture is not looped but is held by stops 25 and 26, when cut it forms two pieces, both of which must be removed.

The suture apertures 20, 20 (FIG. 3) are located adjacent the circumferential edge of the lens. When using a lens of the conventional circular shape, if the lens is or becomes mispositioned or de-centered within the lens pocket, the suture apertures (which remain after removal of the suture retaining means), can be in the field of vision through the lens and can thereby cause distortion. FIG. 10 shows an oval or elliptical lens 40 which has a major diameter that, when the lens is implanted, lies parallel to the patient's spine. The lens is folded on its major axis. The field of vision (through which light is focused when the lens is properly centered) is a central area indicated by dashed line 43, and is typically a circle of about 6.5 mm diameter. On opposite sides of this circular area (above and below it as implanted), are end areas 44, 44, which are contiguous with the circular field of vision and constitute an integral part of the lens. The haptics 11, 12 are attached in the end areas. The apertures or other retaining means 42 are preferably positioned approximately midway between the major and minor axes, in the end areas. The field of vision 43 through the lens does not extend to the position of the attaching means 42. With this lens shape the minor diameter is large enough that vision is not obstructed by the lens edge, even if decentering occurs. Moreover, the retaining means does not affect sight through the lens, either normally or if decentering occurs. The lens is folded along its long axis 41; its width as folded, which is across the short axis, does not reflect its greater length, and the "longer" lens can be inserted through the same size incision (about 3.2 mm) as a conventional circular lens. It should thus be noted that the oval shape is useful, whether or not any retaining means are used to hold the lens folded.

The preferred form of simplified retaining means for use with this invention is the suture ties already described. However, I have also invented alternatives which do not require the application of a separate suture, and which may be made integral with the lens so as to remain in the eye as a part of the lens after implantation. Thee alternatives comprise "post and socket" snaps shown in FIGS. 11 and 12; a T-shaped toggle and slot (FIG. 13) and adhesive means (FIG. 14).

Figure 11:
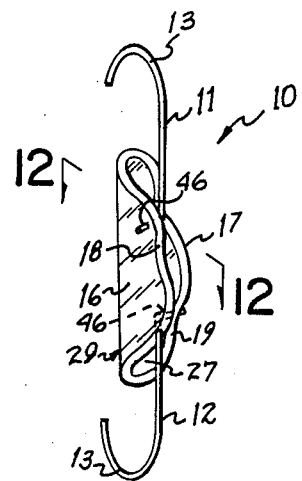
FIG. 11 is a diagrammatic perspective showing a lens having post and socket retaining means, showing the lens in folded retained configuration.
Figure 12:
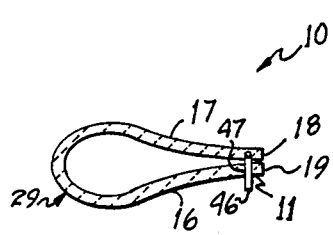
FIG. 12 is a cross-section taken on line 12—12 of FIG. 11.

The post and socket fastening means of FIGS. 11 and 12 comprises a short or "stub" post projecting perpendicularly outward from the surface of the lens, and which may comprise an angularly outturned end 46 of each haptic. In FIG. 11, the end 46 of haptic 11 snaps into or is retained frictionally in an aperture in lens half 16; the end of haptic 12 similarly engages an aperture in lens half 17. Each post is sized to be received frictionally or positively as a snap into an aperture 47 formed in the opposite lens half (FIG. 12). The lens so retained can be released by inserting a blade into the space or gap between the lens halves and twisting it adjacent each latch.

Figure 13:
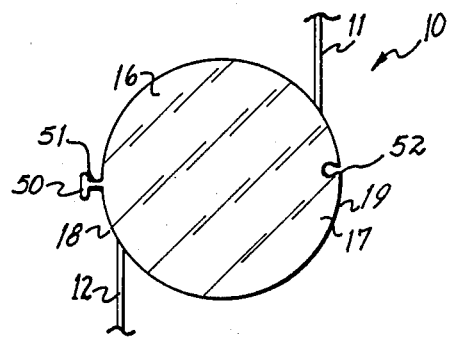
FIG. 13 is an enlarged plan of another alternative embodiment, showing a lens having integral latch and slot retaining means.

The retaining means shown in FIG. 13 is formed integrally with the lens and comprises a flexible T-shaped toggle or latch 50, having a narrow shank 51 projecting from one side of the lens, and a cooperating slot or seat 52 diametrically opposite in the other lens half. In the lens as made the toggle 50 may extend in the plane of the lens and may be formed, as with a die, integrally in the plane of the lens. The latch is flexible and folds or hinges so that when the lens is folded it can be swung or hooked into the latch slot 52 to hold the lens secure. It is released again by the two instrument technique, holding the lens by a forceps while pulling shank 51 out of slot 52. In this embodiment, as in the post and socket embodiment, the latch remains with the lens in the eye.

Figure 14:
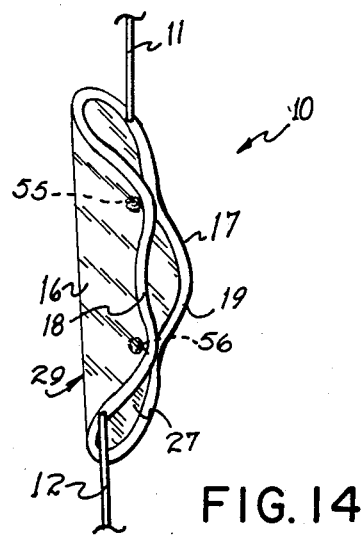
FIG. 14 is a diagrammatic perspective view of another embodiment wherein a lens which is held folded by an adhesive at two points along its overlying edges.

FIG. 14 shows a technique wherein the two lens halves are adhered by dots of low tack adhesive 55, 56 on the lens halves. By "low tack" is meant an adhesive which grips sufficiently to adhere the lens halves together for handling and insertion, but which yields under tension to release the lens halves when the second instrument is inserted between the lens halves and twisted to separate them. Other adhesive means, including hook and pile type material, are also contemplated for use in the invention.

The various aspects of the invention have been described in their preferred embodiments, and those skilled in the art will understand that the invention is not limited to those forms, and extends also to other embodiments within the scope of the claims which follow.

What is claimed is:

1. A folded intraocular lens comprising,
   a resiliently foldable lens which is folded about a central axis of folding so that a first half of the lens overlies a second half thereof and corresponding lens edge portions on each side of the axis of folding are juxtaposed,
   each half of said lens having at least one aperture extending perpendicularly through it adjacent said edge portion, the apertures positioned on the respective lens halves so that the apertures of the folded lens are aligned opposite one another, and
   retaining means holding the lens in such folded configuration, said retaining means comprising a length of suture which extends through and directly between the aligned apertures of the overlying lens halves,
   said retaining means also including a portion which prevents said length of suture from passing through the apertures,
   the resiliency of the lens tending to unfold the lens and holding said length of suture in tension between said apertures.

2. The folded lens of claim 1 wherein said lens is elongated with a major dimension which is greater than its minor dimension, said lens having a generally circular vision area of diameter which is sufficient that, when the lens has been implanted into an eye, it provides an optically unobstructed field of vision through the lens, even if the lens become decentered within the eye,
   said lens also having end portions contiguous with and adjacent to said field of vision and oriented along said major dimension, said end portions lying beyond the field of vision through the lens when implanted,
   at least one said aperture being located in each end portion, outside said field of vision.

3. The folded lens of claim 2 wherein said lens is elliptical, said apertures being located midway between the major and minor dimensions of the lens.

4. The folded lens of claim 3 wherein two such apertures are located on each lens half, the apertures of each half positioned to align with the respective apertures of the other half, and
   two separate lengths of suture extend through the aligned pair of apertures.

5. The folded lens of claim 4 wherein the retaining means is tied on itself as a loop.

6. A folded intraocular lens comprising,
   a resiliently foldable lens which is folded about a central axis of folding so that a first half of the lens overlies a second half thereof and corresponding lens edge portions on each side of the axis of folding are juxtaposed, each half of said lens having at least one aperture extending perpendicularly through it adjacent said edge portion, the apertures positioned on the respective lens halves so that the apertures of the folded lens are aligned opposite one another, and retaining means holding the lens in such folded configuration, said retaining means comprising a length of suture which extends through and directly between the aligned apertures of the overlying lens halves, said retaining means also including a portion which prevents said length of suture from passing through the apertures, the resiliency of the lens tending to unfold the lens and holding said length of suture in tension between said apertures, said lens being elongated with a major dimension which is greater than its minor dimension, and having a generally circular vision area of diameter which is sufficient that, when the lens has been implanted into an eye, it provides an optically unobstructed field of vision through the lens, even if the lens becomes decentered within the eye, said lens also having end portions contiguous with and adjacent to said field of vision and oriented along said major dimension, said end portions lying beyond the field of vision through the lens when implanted, at least one said aperture being located in each end portion, outside said field of vision, said lens being elliptical, said apertures being located between the major and minor dimensions of the lens, two such apertures being located on each lens half, the apertures of each half positioned to align with the respective apertures of the other half, two separate lengths of suture extending through the aligned pair of apertures, each such length of suture forming a loop, said retaining means having stops which abut the outside of the folded lens and thereby prevent the lens from unfolding.

* * * * *